United States Patent [19]
Fishwick et al.

[11] 3,936,437
[45] Feb. 3, 1976

[54] MONOAZO COMPOUNDS DERIVED FROM 2-HYDROXYMETHYL-AMINO BENZOIC ACIDS AND 2,6-DIHYDROXYPYRIDINES

[75] Inventors: Brian Ribbons Fishwick; Colin William Greenhalgh; Nigel Hughes, all of Blackley, England

[73] Assignee: Imperial Chemical Industries Limited, London, England

[22] Filed: Dec. 17, 1973

[21] Appl. No.: 425,278

[30] Foreign Application Priority Data
Dec. 22, 1972 United Kingdom............... 59315/72

[52] U.S. Cl......... 260/156; 260/249.5; 260/294.8 R; 260/294.9; 260/295 R; 260/295 AM; 260/297 Z; 260/343.3 R; 260/518 R
[51] Int. Cl.².......................................... C09B 29/36
[58] Field of Search..................................... 260/156

[56] References Cited
FOREIGN PATENTS OR APPLICATIONS
2,011,018  9/1971  Germany............................ 260/156
2,004,487  8/1971  Germany............................ 260/156

*Primary Examiner*—Charles F. Warren
*Attorney, Agent, or Firm*—Cushman, Darby & Cushman

[57] ABSTRACT

The disperse monoazo dyestuffs, free from sulphonic acid groups, which are represented by the formula:

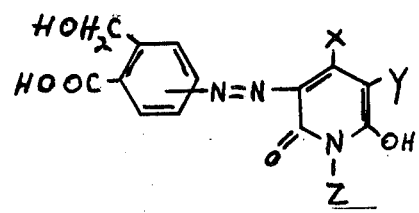

wherein X is alkyl, substituted alkyl, phenyl or optionally substituted carbamoyl; Y is a hydrogen atom or a substituent; and Z is a hydrogen atom or an optionally substituted alkyl, cycloalkyl, aryl or heterocyclic radical or an optionally substituted amino group, a process for the manufacture of the said dyestuffs and their use for coloring synthetic textile materials.

2 Claims, No Drawings

MONOAZO COMPOUNDS DERIVED FROM 2-HYDROXYMETHYL-AMINO BENZOIC ACIDS AND 2,6-DIHYDROXYPYRIDINES

This invention relates to disperse monoazo dyestuffs which are valuable for coloring synthetic textile materials.

According to the invention there are provided the disperse monoazo dyes, free from sulphonic acid groups, which are represented by the formula:

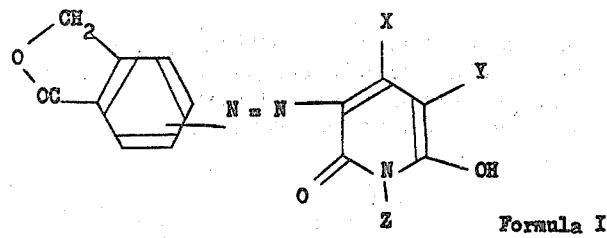

Formula I wherein X is alkyl, substituted alkyl, phenyl or optionally substituted carbamoyl; Y is a hydrogen atom or a substituent; and Z is a hydrogen atom or an optionally substituted alkyl, cycloalkyl, aryl or heterocyclic radical or an optionally substituted amino group.

The pyridone ring present in the said dyestuffs can exist in a number of tautomeric forms. Although the dyestuffs have only been formulated in one of the possible tautomeric forms it is to be understood that the specification includes within its scope the other tautomeric forms of the dyestuffs.

The dyestuffs of Formula I are readily converted in aqueous medium to the dyestuffs of the formula:

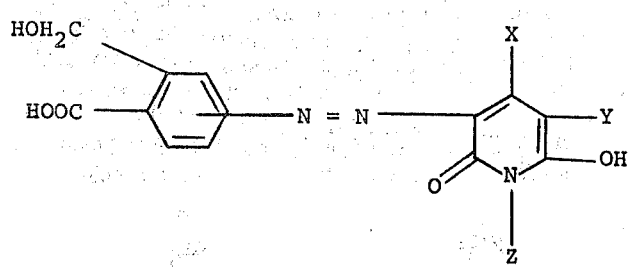

the presence of acid favoring the formation of the structure represented by Formula I containing the lactone ring, whilst the presence of alkali favors the formation of the structure of Formula II by opening the lactone ring. Although for the purpose of simplicity the dyestuffs are formulated as containing the lactone ring it is to be understood that the dyestuffs in which the lactone ring has been opened are also within the scope of the invention.

Throughout this specification the terms "lower alkyl" and "lower alkoxy" are used to denote alkyl and alkoxy radicals respectively containing from 1 to 4 carbon atoms.

As examples of the alkyl radicals represented by Z there may be mentioned alkyl radicals containing from 1 to 12 carbon atoms such as methyl, ethyl, propyl, butyl, amyl, hexyl, octyl, decyl and dodecyl radicals. The substituted alkyl radicals represented by Z are preferably substituted lower alkyl radicals for example hydroxy lower alkyl such as β-hydroxyethyl, lower alkoxy lower alkyl such as β-ethoxyethyl and γ-methoxypropyl, phenyl lower alkyl such as benzyl and β-phenylethyl, cyano lower alkyl such as β-cyanoethyl, lower alkoxycarbonyl lower alkyl such as ethoxycarbonylmethyl and β-(methoxycarbonyl)ethyl, lower alkylcarbonyloxy lower alkyl such as β-acetoxyethyl, chloro lower alkyl such as β-chloroethyl, phenoxy lower alkyl such as β-phenoxyethyl, phenylthio lower alkyl such as β-phenylthioethyl, lower alkyl substituted by heterocyclic radicals such as β-pyrid-2-ylethyl and β-tetrahydrofur-2-ylethyl, monocyclic arylcarbonyloxy lower alkyl such as β-(benzoyloxy)ethyl and β-(m-methylbenzoyloxy)ethyl, acyl lower alkyl such as benzoylmethyl, lower alkylcarbonyl lower alkyl such as acetylmethyl and β-acetylethyl, phenylsulphonylmethyl and β-(ethylsulphonyl)ethyl, and amino lower alkyl and N-substituted derivatives thereof such as β-aminoethyl, γ-dimethylaminopropyl, β-(acetylamino)ethyl, β-(benzoylamino)ethyl and β-succinimidoethyl. As examples of the aryl and substituted aryl radicals represented by Z there may be mentioned phenyl, tolyl, xylyl, anisyl, chlorophenyl and bromophenyl. As an example of a cycloalkyl radical represented by Z there may be mentioned cyclohexyl. As examples of the substituted amino groups represented by Z there may be mentioned arylamino and substituted arylamino radicals such as anilino, anisidino, toluidino, chloroanilino and bromanilino, but more especially N-lower alkylamino and N:N-di lower alkylamino such as methylamino, diethylamino and N-methyl-N-n-propylamino, and also benzylamino and cyclohexylamino radicals. As examples of the heterocyclic radicals represented by Z there may be mentioned pyrid-2-yl and fur-2-yl radicals. It is however preferred that Z represents a hydrogen atom, an alkyl radical of from 1 to 12 carbon atoms, a substituted lower alkyl radical in particular a hydroxy lower alkyl or lower alkoxy lower alkyl radical, or an optionally substituted phenyl radical.

The alkyl radicals represented by X are preferably lower alkyl radicals such as methyl, ethyl, propyl and butyl. The substituted alkyl radicals represented by X are preferably substituted lower alkyl radicals such as phenyl lower alkyl for example benzyl, cyano lower alkyl such as cyanomethyl, lower alkoxy lower alkyl such as β-methoxyethyl, phenoxy lower alkyl such as β-phenoxyethyl, lower alkyl substituted by heterocyclic radicals such as pyrid-2-ylmethyl and thiazol-2- ylmethyl, and lower alkoxycarbonyl lower alkyl such as ethoxycarbonylmethyl. The substituted carbamoyl radicals represented by X are preferably N-lower alkyl carbamoyl and N:N-di lower alkyl carbamoyl such as N-methylcarbamoyl and N:N-diethylcarbamoyl. It is however preferred that X represents the methyl radical.

As examples of the substituents represented by Y there may be mentioned chlorine, bromine, cyano, lower alkyl carbonyl such as acetyl, benzoyl, lower alkyl sulphonyl such as ethylsulphonyl, monocyclic aryl sulphonyl such as benzenesulphonyl, lower alkoxy carbonyl such as methoxy carbonyl and ethoxycarbonyl, phenoxycarbonyl, carbamoyl and N-lower alkyl and N:N-di lower alkyl derivatives thereof such as N-ethyl-carbamoyl and N:N-dimethylcarbamoyl, sulphamoyl and N-lower alkyl and N:N-di lower alkyl derivatives thereof such as N-methyl-sulphamoyl and N:N-diethyl-sulphamoyl, lower alkyl such as methyl, ethyl, propyl and butyl, and amino lower alkyl and substituted derivatives thereof such as β-aminoethyl, N-methylaminomethyl and N-acetyl-N-methylaminomethyl. It is however preferred that Y represents the cyano group.

According to a further feature of the invention there is provided a process for the manufacture of the monoazo dyestuffs of the invention which comprises diazotizing an amine of the formula:

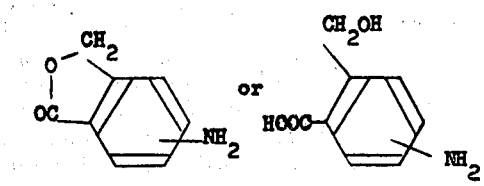

and coupling the resulting diazo compound with a coupling component which, in one of the possible tautomeric forms, is of the formula:

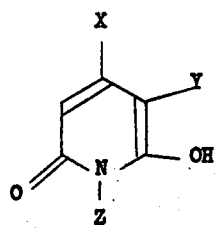

wherein X, Y and Z have the meanings stated.

The process of the invention can be conveniently carried out by adding sodium nitrite to a solution or suspension of the said amine in a dilute aqueous solution of hydrochloric acid and adding the resulting solution or suspension of the diazo compound to a solution of the coupling component in an aqueous solution of sodium hydroxide, the pH of the resulting mixture being adjusted, if necessary, so as to facilitate the coupling reaction. After coupling is completed the resulting azo dyestuff is isolated in conventional manner.

As specific examples of the said amines there may be mentioned 4- or 5-amino-2-hydroxymethylbenzoic acid.

The said coupling components can themselves be obtained by a number of methods, such as are described, for example, in "Heterocyclic Compounds — Pyridine and its derivatives — Part 3" which was edited by Klingsberg and published by Interscience Publishers in 1962. Typical methods include, for example, (1) condensing together compounds of the formulae: XCOCH$_2$COOalkyl and Y-CH$_2$COOalkyl in the presence of an excess of an amine of the formula Z-NH$_2$; (2) cyclization of an α:β-disubstituted glutaconamide of the formula:

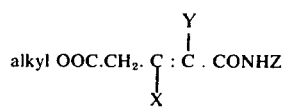

which is itself obtained by condensing together in the presence of a basic catalyst compounds of the formula X.CO.CH$_2$COOalkyl and Y.CH$_2$.CONHZ: (3) cyclization of an α:β-disubstituted glutaconamide of the formula:

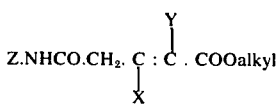

which is itself obtained by condensing together in the presence of a basic catalyst compounds of the formula XCO.CH$_2$CONHZ and YCH$_2$.COOalkyl.

As specific examples of the said coupling components there may be mentioned 1-(methyl, ethyl, n-propyl, n-butyl, n-hexyl, n-octyl, n-decyl, n-dodecyl, β-hydroxyethyl, γ-methoxypropyl, cyclohexyl, benzyl, phenyl, tolyl, xylyl or anisyl)-3-(cyano or carbonamido)-4-methyl-6-hydroxypyrid-2-one, 3-cyano-4-methyl-6-hydroxypyrid-2-one, 1:4-dimethyl-3-carbonamido-6-hydroxypyrid-2-one, 1:4-dimethyl-6-hydroxypyrid-2-one, and 1-(amino, methylamino, diethylamino, anilino, cyclohexylamino or benzylamino)-3-(cyano- or carbonamido)-4-methyl-6-hydroxypyrid-2-one.

A preferred class of the dyestuffs of the invention comprises the monoazo dyestuffs of the formula

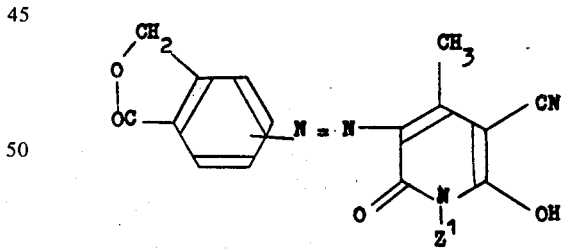

wherein Z$^1$ is a hydrogen atom, an alkyl radical of from 1 to 12 carbon atoms, a substituted lower alkyl radical, preferably hydroxy lower alkyl or lower alkoxy lower alkyl, or an optionally substituted phenyl radical. Preferably the azo group is attached to the benzene ring in para position to the -CO- group of the lactone ring.

The monoazo dyestuffs of the invention are valuable for coloring textile materials, in particular synthetic textile materials such as polyamide textile materials (Nylon 6 and Nylon 6:6), cellulose acetate textile materials (cellulose triacetate and secondary cellulose acetate), and preferably aromatic polyester textile material such as polyethylene terephthalate textile materials, and this use of the dyestuff forms a further feature of the present invention.

According to a further feature of the invention there is provided a process for coloring synthetic textile materials which comprises applying to the said textile materials by a dyeing, padding or printing process an aqueous dispersion of at least one monoazo dyestuff as hereinbefore defined.

The methods by which the said dyestuffs are applied to synthetic textile materials can be any of the dyeing, padding or printing methods which are conventionally employed in applying disperse dyestuffs to synthetic textile. Thus, for example, dyeing can be carried out by immersing the synthetic textile material in a dyebath containing an aqueous dispersion of the said dyestuff, and then carrying out the dyeing at an appropriate temperature, for example at temperatures in the region of 85°C for secondary cellulose acetate textile materials, at 90° – 100°C in the case of polyamide textile materials, at temperatures in the region of 100°C for polyester and cellulose triacetate textile materials when the dyebath additionally contains a carrier, or at temperatures in the region of 120° – 140°C when a carrier is not required.

Padding can be conveniently carried out by continuously passing the synthetic textile material through a padding liquor containing an aqueous dispersion of the said dyestuff, excess liquor then being removed by passing the material through a padding mangle. The padded textile material is then dried and subjected to the action of steam or to a dry heat treatment.

Printing can be conveniently carried out by applying a print paste containing an aqueous dispersion of the said dyestuff to the textile material by any of the methods conventionally employed in applying print pastes to textile materials, for example by screen or roller printing. The printed textile material is then dried and subjected to the action of steam or to a dry heat treatment.

At the conclusion of the above processes the textile material is rinsed in water optionally containing soap or a synthetic detergent and then dried. In the case of aromatic polyester textile material it is also preferred to give the colored textile material a rinse in a warm dilute aqueous solution of an alkali such as sodium carbonate in order to remove any unfixed dyestuff from the surface of the textile material.

The said dyebaths, print pastes or padding liquors can contain any of the adjuvants which are commonly present in such systems, for example anionic, non-ionic and/or cationic dispersing agents, urea, acids such as acetic acid or formic acid, thickeners such as sodium alginate, natural gums and water-in-oil emulsions, organic liquids such as benzyl alcohol, and carriers such as diphenyl, hydroxydiphenyl, methylsalicylate and $\beta$-methylnaphthalene.

The aqueous dispersions of the said dyestuffs which are used in the dyebaths, padding liquors or print pastes can be prepared in conventional manner by milling the dyestuffs in water in the presence of a dispersing agent. Alternatively the said dispersions can be formed by dissolving the dyestuffs in aqueous alkaline media, incorporating such solutions into the dyebath, print pastes or padding liquors and then acidifying by addition of an acid such as acetic acid or formic acid. This acidification is preferably carried out before the said systems are applied to the textile material, but, if desired, the said systems containing the dyestuff in soluble form can be applied to the textile material and then acidified or the textile material subjected to a separate treatment with an acid.

The textile materials which can be colored by the process of the invention can be in the form of fibres, filaments or woven or knitted goods. If desired the synthetic textile materials can be in the form of unions with other textile materials, for example polyester/cotton and polyester/wool unions, in which event the dyestuffs of the present invention are preferably used in conjunction with suitable dyestuffs, for example Reactive Dyes, Vat Dyes or Acid Dyestuffs, for the other textile material.

When applied to synthetic textile materials the dyestuffs of the invention yield greenish-yellow to orange shades which possess excellent fastness to the tests which are conventionally applied to such textile materials. The dyestuffs also have excellent build-up properties on polyester textile materials so that heavy depths of shade can be readily obtained.

The invention is illustrated but not limited by the following Examples in which the parts and percentages are by weight:

EXAMPLE 1

A solution of 1.7 parts of 2-hydroxymethyl-4-aminobenzoic acid in a mixture of 25 parts of water and 12.5 parts of a 2N aqueous solution of hydrochloric acid is cooled to 0° – 5°C and 5 parts of a 2N aqueous solution of sodium nitrite are added. The mixture is stirred for 30 minutes and is then added to a solution of 1.8 parts of 1-ethyl-3-cyano-4-methyl-6-hydroxypyrid-2-one and 5 parts of sodium acetate in 50 parts of water containing 5 parts of a 2N aqueous solution of sodium hydroxide at 5°C. The mixture is stirred for 15 minutes and the precipitated yellow dyestuff is filtered off, washed with water and dried. The dyestuff has a melting point of 317°C.

The 2-hydroxymethyl-4-aminobenzoic acid used in the above Example was itself obtained by treatment of 4-nitrophthalimide with a zinc/copper complex in a boiling aqueous solution of sodium hydroxide. Similar dyestuffs are obtained when the 2-hydroxymethyl-4-aminobenzoic acid used in the above Example is replaced by 2-hydroxymethyl-3- or 6-aminobenzoic acid.

EXAMPLE 2

0.1 Part of the yellow dyestuff of Example 1 is dissolved in 100 parts of water containing 0.04 part of sodium hydroxide and the pH is then adjusted to 4 by the addition of formic acid. 10 Parts of a polyethylene terephthalate textile material are immersed in the resulting dyebath and dyeing is then carried out for 45 minutes at 130°C in a closed vessel. The dyed textile material is then removed from the dyebath, rinsed in water, immersed for 10 minutes in a 0.1% aqueous solution of sodium carbonate at 50°C, rinsed again in water and finally dried. A greenish-yellow dyeing of excellent fastness to light, to wet treatments, to rubbing and to dry heat treatments is obtained.

EXAMPLE 3

In place of the 1.7 parts of 2-hydroxymethyl-4-aminobenzoic acid used in Example 1 there are used 1.7 parts of 2-hydroxymethyl-5-aminobenzoic acid and in place of the 1.8 parts of 1-ethyl-3-cyano-4-methyl-6-hydroxypyrid-2-one used in Example 1 there are used 2.1 parts of 1-n-butyl-3-cyano-4-methyl-6-hydroxypyrid-2-one. A greenish-yellow dyestuff is obtained.

In place of the 1.8 parts of the coupling component used in Example 1 there are used equivalent amounts of the coupling components of the formula

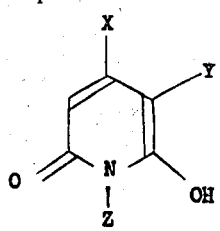

the symbols of which have the values given in the respective columns of the following Table. The last column of the table lists the shades obtained when the dyestuffs are applied to an aromatic polyester textile material.

| EXAMPLE | Z | Y | X | SHADE |
|---|---|---|---|---|
| 4 | n-butyl | cyano | methyl | Greenish-yellow |
| 5 | hydrogen | " | " | " |
| 6 | methyl | " | " | " |
| 7 | n-propyl | " | " | " |
| 8 | iso-propyl | " | " | " |
| 9 | n-pentyl | " | " | " |
| 10 | n-hexyl | " | " | " |
| 11 | n-octyl | " | " | " |
| 12 | β-ethylhexyl | " | " | " |
| 13 | n-dodecyl | " | " | " |
| 14 | γ-methoxy-propyl | " | " | " |
| 15 | β-hydroxy-ethyl | " | " | " |
| 16 | β-acetoxy-ethyl | " | " | " |
| 17 | γY-ethoxy-propyl | " | " | " |
| 18 | ethoxy-carbonyl-methyl | " | " | " |
| 19 | cyclohexyl | " | " | " |
| 20 | β-phenylethyl | " | " | " |
| 21 | β-pyrid-2-yl-ethyl | " | " | " |
| 22 | β-chloroethyl | " | " | " |
| 23 | β-phenoxyethyl | " | " | " |
| 24 | β-phenylthio-ethyl | " | " | " |
| 25 | β-tetrahydro-fur-2-yl ethyl | " | " | " |
| 26 | β-cyanoethyl | " | " | " |
| 27 | β-(β'-cyano-ethoxy)ethyl | " | " | " |
| 28 | γ-(benzyl-carbonyloxy)propyl | " | " | " |
| 29 | β-(phenoxy-methyl-carbonyloxy)ethyl | " | " | " |
| 30 | β-(m-methyl-benzyloxy)ethyl | " | " | " |
| 31 | β-(phenoxy-carbonyloxy)ethyl | " | " | " |
| 32 | β-(dimethyl-aminocarbonyl-oxy)ethyl | " | " | " |
| 33 | acetylmethyl | " | " | " |
| 34 | benzoylmethyl | " | " | " |
| 35 | β-(phenyl sulphonyl)ethyl | " | " | " |
| 36 | tetrahydro-1:1-dioxo-thiophen-3-yl | " | " | " |
| 37 | β-(benzoyl-amino)ethyl | " | " | " |
| 38 | β-succinimi-doethyl | " | " | " |
| 39 | benzyl | " | " | " |
| 40 | m-tolyl | " | " | " |
| 41 | p-anisyl | " | " | " |
| 42 | m-chlorophenyl | " | " | " |
| 43 | amino | " | " | Yellow |
| 44 | anilino | " | " | " |
| 45 | methylamino | " | " | " |
| 46 | dimethylamino | " | " | " |
| 47 | benzylamino | " | " | " |
| 48 | cyclohexylamino | " | " | " |
| 49 | tetrahydrox-4:4-dioxo 1:4-thiazin-4-yl | " | " | " |
| 50 | m-toluidino | " | " | " |

-continued

| EXAMPLE | Z | Y | X | SHADE |
|---|---|---|---|---|
| 51 | pyrid-4-ylamino | " | " | " |
| 52 | thiazol-2-ylamino | " | " | " |
| 53 | 2:4-dimethoxy-1:3:5-triazin-6-ylamino | " | " | " |
| 54 | phenyl | " | " | Greenish-yellow |
| 55 | ω-(isobutyroxy)butyl | " | " | " |
| 56 | ethyl | hydrogen | " | " |
| 57 | " | methyl | " | " |
| 58 | " | butyl | " | " |
| 59 | " | carbamoyl | " | " |
| 60 | butyl | methyl-sulphonyl | " | " |
| 61 | ethyl | phenyl-sulphonyl | " | " |
| 62 | " | N:N-dimethyl-sulphamoyl | " | " |
| 63 | " | N:N-dimethyl-carbamoyl | " | " |
| 64 | " | piperidino sulphonyl | " | " |
| 65 | " | ethoxy-carbonyl | " | " |
| 66 | " | acetyl | " | " |
| 67 | butyl | N-methyl-carbamoyl | " | " |
| 68 | methyl | benzoyl | " | " |
| 69 | " | bromo | " | Yellow |
| 70 | butyl | chloro | " | " |
| 71 | ethyl | N-methyl-aminomethyl | " | " |
| 72 | " | N-acetyl-N-methylamino-methyl | " | " |
| 73 | methyl | cyano | phenyl | Greenish-yellow |
| 74 | " | " | isobutyl | " |
| 75 | hydrogen | " | β-phenylethyl | " |
| 76 | ethyl | " | β-methoxyethyl | " |
| 77 | ethyl | " | ethyl | " |
| 78 | butyl | " | cyanomethyl | " |
| 79 | ethyl | " | β-phenoxy-ethyl | " |
| 80 | " | " | pyrid-2-yl-methyl | " |
| 81 | " | " | thiazol-2-ylmethyl | " |
| 82 | " | " | fur-2-yl-methyl | " |
| 83 | " | " | ethoxycarbon-ylmethyl | " |
| 84 | " | " | N:N-dimethyl-carbamoyl | " |

We claim:
1. A disperse monoazo dyestuff free from sulphonic acid groups having the formula

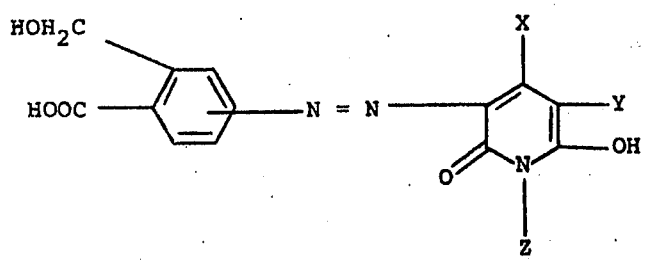

wherein X is selected from the group consisting of lower alkyl, phenyl, phenyl lower alkyl linked to the pyridone ring through said lower alkyl, lower alkoxy lower alkyl, cyano lower alkyl, phenoxy lower alkyl, lower alkoxy carbonyl lower alkyl and N:N-di(lower alkyl) carbamoyl; Y is selected from the group consisting of cyano, hydrogen, lower alkyl, carbamoyl, N-lower alkyl carbamoyl, N:N-di(lower alkyl) carbamoyl, lower alkyl sulphonyl, phenylsulphonyl, sulphamoyl, N-lower alkyl sulphamoyl, N:N-di(lower alkyl) sulphamoyl, lower alkoxycarbonyl, lower alkylcarbonyl, benzoyl, bromine, chlorine and lower alkylamino lower alkyl; and Z is selected from the group consisting of hydrogen, alkyl having from 1 to 12 carbon atoms, lower alkoxy lower alkyl, hydroxy lower alkyl, lower alkylcarbonyloxy lower alkyl, lower alkoxycarbonyl lower alkyl, cyclohexyl, phenyl lower alkyl linked to the pyridone ring through said lower alkyl, chloro lower alkyl, phenoxy lower alkyl, phenylthio lower alkyl, cyano lower alkyl, cyano lower alkoxy lower alkyl, benzyl carbonyloxy lower alkyl, phenoxy carbonyloxy lower alkyl, lower alkylcarbonyl lower alkyl, benzoyl lower alkyl, phenylsulphonyl lower alkyl, benzoylamino lower alkyl, phenyl, tolyl, anisyl, chlorophenyl, amino, N-lower alkylamino, N:N-di(lower alkyl) amino, anilino, toluidino, benzylamino and cyclohexylamino.

2. A dyestuff as claimed in claim 1 having the formula

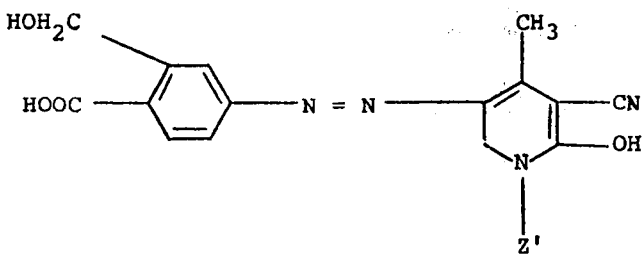

wherein Z' is selected from the group consisting of hydrogen, alkyl having from 1 to 12 carbon atoms, hydroxy lower alkyl, lower alkoxy lower alkyl, phenyl, chlorophenyl, tolyl and anisyl.

* * * * *